United States Patent
Bewert et al.

(10) Patent No.: US 6,328,995 B1
(45) Date of Patent: Dec. 11, 2001

(54) STABLE VITAMIN AND/OR CAROTENOID PRODUCTS IN POWDER FORM AND PROCESS FOR THEIR PRODUCTION

(75) Inventors: Wolfgang Bewert, Frankenthal; Roland Betz, Niederkirchen; Peter Schmitt, Ludwigshafen, all of (DE); David Kenneth Bower, Trenton; Frederick Kenneth Chaundy, Grosse Ile, both of MI (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/404,600

(22) Filed: Sep. 24, 1999

(51) Int. Cl.⁷ .............................. A61K 9/14; A61K 9/50; A61K 31/07; A61K 31/27; A61K 31/355

(52) U.S. Cl. ..................... 424/489; 424/499; 514/725; 514/458; 514/474

(58) Field of Search .................... 568/824; 549/408; 424/489, 499; 514/725, 458, 474

(56) References Cited

U.S. PATENT DOCUMENTS 4,929,774 * 5/1990 Fukamachi et al. ................. 568/824

* cited by examiner

*Primary Examiner*—Thurman K. Page
*Assistant Examiner*—Amy E Pulliam
(74) *Attorney, Agent, or Firm*—Keil & Weinkauf

(57) ABSTRACT

Stable dry powders which are insoluble in hot water and which contain one or more lipid-soluble vitamins an/or one or more carotenoids are formed in an aqueous dispersion containing 2 to 50% by weight of at least one protein, 1 to 30% by weight of at least one sugar, 0.2 to 20% by weight of $K_2HPO_4$, $Na_2HPO_4$ or mixtures thereof, 0.1 to 20% by weight of at least one lipoid-soluble vitamin and/or at least one carotenoid and 5 to 95% of water. This dispersion is converted into dry powder which is heated in the range of 55° C. to 1800° C.

14 Claims, No Drawings

STABLE VITAMIN AND/OR CAROTENOID PRODUCTS IN POWDER FORM AND PROCESS FOR THEIR PRODUCTION

Stable vitamin and/or carotenoid products in powder form and process for their production.

The invention relates to stable vitamin and/or carotenoid products in powder form and to a process for their preparation.

Vitamin and carotenoid products in powder form are generally known and are used on a large scale in the pharmaceutical industry and in animal feed and human food industries. Thus, many processes for producing suitable products are described in the literature.

As a rule, the lipid-soluble vitamins and/or carotenoids are dispersed in an aqueous solution of an organic film-forming colloid and the resulting dispersion is finally converted into dry products in powder form.

Gelatin is normally used as film-forming colloid in the prior art.

The stability of products of this type must meet particularly high demands when they are intended to be used as additives to human foods or animal feeds because in this use they are exposed to a high variety of effects such as elevated temperatures, humidity, mechanical friction or pressure which are extremely harmful for the sensitive vitamins and carotenoids. There has thus been no lack of attempts to develop processes providing particularly thermally and mechanically stable products.

Thus, for example, GB 993 138 discloses the stabilization of gelatin-containing vitamin products, the particles being treated with a gelatin-denaturing agent such as formaldehyde, glyoxal, acetaldehyde or dihydroxyacetone, and then being heated or else only subjected to a heat treatment.

EP-B-0 285 682 discloses a process for producing spherical products which contain lipid-soluble vitamins, by forming an emulsion using water, gelatin and a sugar, converting the emulsion into droplets, collecting the droplets in a starch powder composition in such a way that the droplets remain separated from one another until better shape has been permanently formed, separating the resulting particles from excess starch powder and then treating with heat at temperatures of from 90 to 180° C.

In addition, EP-A-0 494 417 describes a process for crosslinking gelatin in the presence of a reducing sugar and of a water-soluble salt of a carboxylic acid or of an inorganic acid at temperatures in the range from 55 to 180° C.

However, the abovementioned processes have the disadvantage that the required crosslinking times are often too long or the crosslinking temperatures are too high so that there may be damage to the thermally unstable lipid-soluble vitamins or carotenoids in the product.

It is an object of the present invention to provide a process for producing stable vitamin and/or carotenoid products in powder form which do not have the abovementioned disadvantages.

We have found that this object is achieved by a process for producing stable dry powders which are insoluble in hot water and which contain one or more lipid-soluble vitamins and/or one or more carotenoids, which comprises the following process steps:

A. preparation of an aqueous dispersion containing:
   a1) 2 to 50% by weight of at least one protein,
   a2) 1 to 30% by weight of at least one sugar,
   a3) 0.2 to 20% by weight of at least one inorganic salt,
   a4) 0.1 to 20% by weight of at least one lipid-soluble vitamin and/or at least one carotenoid,
   a5) 5 to 95% by weight of water,
   where all the % by weight data are based on the total weight of the aqueous dispersion, and the total of the percentage data for the individual components a1) to a5) is 100%,
B. converting this dispersion into a dry powder and
C. heating the dry powder to a temperature in the range from 55° C. to 180° C.,
   wherein alkali metal phosphates are used as inorganic salt a3), so that the protein is crosslinked to an extent such that the dry powder is insoluble in water for at least 3 minutes after introduction into water at 100° C.

The proteins a1) employed as protective colloid in the preparation of the aqueous dispersion in process step (A) may be both of vegetable and of animal origin. Examples which may be mentioned are, in particular, gelatin, inter alia bone gelatin, bovine gelatin, fish gelatin, in each case of the A and B type in a wide bloom range, and pectin, casein or caseinate, soyabean proteins and corn proteins. The gelatins preferably used have a bloom value of from 50 to 300, particularly preferably from 80 to 150. The protective colloid is generally used in amounts of about 2 to 50% by weight, preferably 3 to 25% by weight, particularly preferably 5 to 15% by weight, based on the total weight of the aqueous dispersion.

It is possible to use as component a2) all reducing sugars or sugar syrups containing reducing sugars. Reducing sugars include fructose, glucose, lactose, maltose, xylose, arabinose, ribose and sucrose, and honey and fructose and glucose syrups.

Sugars preferably used for the purpose of the invention are fructose, glucose and sucrose and mixtures thereof. Glucose and/or fructose are particularly preferred sugars. The sugars are generally used in amounts of about 1 to 30% by weight, preferably 2 to 20% by weight, particularly preferably 3 to 15% by weight, based on the total weight of the aqueous dispersion.

The lipid-soluble vitamins of component a4) include vitamins A, E, D and K, including derivatives thereof, for example vitamin A esters such as vitamin A acetate, vitamin A propionate or vitamin A palmitate, and vitamin E esters such as tocopheryl acetate. For the purpose of the invention they can be employed in the form of vitamin solutions in oils, as provitamins and as pure vitamins of natural or synthetic origin. Vitamin A and its derivatives are of particular interest, particularly preferably vitamin A acetate, vitamin A propionate and vitamin A palmitate and mixtures thereof, very particularly preferably vitamin A acetate.

Carotenoids are understood as meaning compounds such as β-carotene, lycopine, bixine, zeaxanthine, citranaxanthine, canthaxanthine, astaxanthine, lutein, capsanthin, cryptoxanthine, β-apo-8'-carotenoic acid and its esters, β-apo-8'-carotenal, β-apo-12'-carotenal and mixtures thereof. Preferred carotenoids are β-carotene, lycopine, lutein, zeaxanthine, canthaxanthine and astaxanthine.

The contents of vitamins and/or carotenoids are generally from 0.1 to 20% by weight, preferably 1 to 15% by weight, particularly preferably 2 to 12% by weight, based on the total weight of the aqueous dispersion obtainable by process step (A).

According to the invention at least one alkali metal phosphate is employed as inorganic salt a3) for preparing the abovementioned aqueous dispersion. Possible examples thereof are sodium, potassium or lithium salts both of mono-, di- and triphosphoric acids and of polyphosphoric acid.

Preferred alkali metal phosphates are tertiary sodium phosphate, sodium dihydrogen phosphate, disodium hydrogen phosphate, disodium dihydrogen diphosphate, pentasodium triphosphate, sodium trimethaphosphate [sic], tertiary potassium phosphate, potassium dihydrogen phosphate, dipotassium hydrogen phosphate, dipotassium hydrogen diphosphate, pentapotassium triphosphate, potassium trimethaphosphate [sic]. Tertiary sodium phosphate, sodium dihydrogen phosphate, disodium hydrogen phosphate, tertiary potassium phosphate, potassium dihydrogen phosphate and dipotassium hydrogen phosphate are particularly preferred. Disodium hydrogen phosphate is very particularly preferred.

The contents of alkali metal phosphate are generally from 0.2 to 20% by weight, preferably 0.3 to 15% by weight, particularly preferably 0.4 to 10% by weight, very particularly preferably 0.5 to 5% by weight, based on the total weight of the aqueous dispersion obtainable by process step (A).

In addition to the abovementioned constituents, it is possible and advantageous to add to the dispersion other auxiliaries and additives customary for producing dry powders of active substances.

Particularly important for use of the dry powders as animal feed additive when the active substances are sensitive to oxidation is addition of antioxidants such as ethoxyquin, butylated hydroxytoluene (BHT), butylated hydroxyanisole (BHA) or, where appropriate, tocopherol, and stabilizers such as citric acid or phytic acid and their alkali metal or alkaline earth metal salts, or else complexing agents such as ethylenediaminetetraacetic acid (EDTA) or nitrilotriacetic acid (NTA).

However, humectants such as glycerol, sorbitol or polyethylene glycols or else additional emulsifiers such as lecithin are frequently also added to the emulsion.

Moreover, additions such as starch, in particular corn starch or maltodextrin, or thickeners such as gum arabic, guar gum, alginates and certain degraded starches have proven beneficial for adjusting the viscosity of the emulsion.

It has emerged that it is advantageous to add as additional compound a6) to the aqueous dispersion in process step (A) from 0.5 to 20% by weight, preferably 1 to 10% by weight, of starch, in particular corn starch.

For further details of the said ligands, nature and amount of such additions, reference may be made to the appropriate specialist literature, for example to the abovementioned monograph "Fat-soluble Vitamins", Vol. 9, in particular pages 128 to 133.

A particular embodiment of the process according to the invention comprises employing in step (A)

a1) 5 to 15% by weight of a gelatin with a bloom value of from 50 to 300, a2) 3 to 15% by weight of at least one sugar selected from the group consisting of fructose and glucose, a3) 0.5 to 5% by weight of $Na_2HPO_4$, a4) 2 to 12% by weight of at least one lipid-soluble vitamin selected from the group consisting of vitamin A, vitamin A acetate, vitamin E and vitamin E acetate, a5) 30 to 85% by weight of water and a6) 1 to 10% by weight of starch.

The general procedure for the process according to the invention is, in order to prepare the dispersion in process step (A), to dissolve at least one protein a1) in hot water at a temperature of from 50 to 70° C., to add to this solution at least one in each case of a sugar a2), an alkali metal phosphate a3), a lipid-soluble vitamin and/or carotenoid, stabilizers and the other conventional additives and, where appropriate, additionally water, and to disperse the mixture by vigorous stirring at elevated temperature. For the thermal crosslinking of the powder which takes place in the last processing step (C), the finished dispersion should be in a pH range of from 4 to 10, preferably 5 to 8, which can be adjusted where appropriate by adding bases such as NaOH, KOH, $Ca(OH)_2$, MgO, sodium carbonate or $NH_4OH$.

The subsequent further processing of the dispersion to give the powders according to the invention can take place by processes known from the literature.

Because of the required particle size distribution of the powder (0.1 to 0.6 mm diameter), preferred processes are those in which precautions are taken that the gelatinized droplets of the dispersion remain separated from one another until their shape has stabilized.

Mention may be made, for example, of the process disclosed in EP-B-74 050, in which the dispersion is sprayed into hydrophobic silica or a metal salt of a higher fatty acid, or else the process disclosed in EP-B-285 682, in which the dispersion is sprayed into starch powder. It has emerged that the spraying with hydrophobic silica as dusting agent can be carried out particularly advantageously.

The powders produced by the described process have after drying (process step B) a water content in the range from 5 to 15% by weight, preferably in the range from 5 to 10% by weight. The products in powder form obtained in this way consist of particles with a well-formed surface. They rapidly dissolve in warm water at about 40° C. to give a milky dispersion.

The thermal curing of the dried powders takes place in process step (C) by heating at temperatures of from 55 to 180° C., the speed of the crosslinking process which can take place increasing with increasing temperature. The crosslinking is preferably carried out at temperatures of from 70 to 130° C., particularly preferably from 85 to 125° C., in a reaction time of from 5 minutes to 3 hours, preferably 6 to 25 minutes.

The powders produced in this way have a water content in the range from 0.1 to 4% by weight, preferably 0.5 to 3.5% by weight, particularly preferably in the range from 1 to 3% by weight, are insoluble in water for at least 3 minutes after introduction into boiling water and have excellent stability on storage (see in this connection Example 2 and Table 2) and in practical applications such as extrusion and pelleting.

Compared with crosslinking processes known in the prior art, the advantage of the alkali metal phosphates used according to the invention as crosslinking aids is that the crosslinking times are shorter (see in this connection Table 1) and the procedure is less stressful for the product. Compared with the use of sodium acetate described in EP-A-0 494 417, with which similar crosslinking times can be achieved, the dry powders produced according to the invention are considerably more stable on storage. It is thus possible to avoid unwanted odor formation both during the crosslinking reaction and during storage—for example by liberation of acetic acid in the case of sodium acetate.

The invention also relates to stable dry powders which are insoluble in hot water according to the process described at the outset, comprising:

a1) 10 to 70% by weight of at least one protein, a2) 5 to 30% by weight of at least one sugar, a3) 0.5 to 25% by weight of at least one alkali metal phosphate, a4) 0.1 to 60% by weight of at least one lipid-soluble vitamin and/or at least one carotenoid, a5) 0.1 to 4% by weight of water, where all the % by weight data are based on the total weight of the dry powder, and the total of the percentage data for the individual components a1) to a5) is 100%.

For a more accurate definition of the individual components a1) to a5)—both in the general and in the preferred embodiment—reference may be made to the statements made at the outset.

Besides constituents a1) to a5), the dry powder according to the invention may additionally contain as component a6) from 0.5 to 40% by weight of starch.

Preferential mention is made for the purpose of the invention of a dry powder comprising a1) 10 to 70% by weight of a gelatin with a bloom value of from 50 to 300, which is crosslinked to an extent such that it is insoluble in water for at least 3 minutes after introduction into water at 100° C., a2) 5 to 30% by weight of at least one sugar selected from the group consisting of fructose and glucose, a3) 0.5 to 10% by weight of $Na_2HPO_4$, a4) 1 to 50% by weight of a compound selected from the group consisting of vitamin A, vitamin A ester, vitamin E and vitamin E ester, a5) 1 to 3% by weight of water.

The invention further relates to human foods or animal feeds which comprise the abovementioned stable dry powders which are insoluble in hot water. By animal feeds are meant in this connection all types of vitamin premixes, premixes, mineral feeds and compound feeds.

The subject matter of the present invention is to be explained in more detail by means of the following examples.

EXAMPLE 1
Production of Vitamin a Dry Powder 34.1 g (30 g of solids) of gelatin A 100 bloom were added to 300 g of water and, after swelling for 30 minutes, dissolved by heating to 60° C. Addition of 21.1 g of fructose syrup (15 g of solids, sugar content 70%, of which 95% fructose in dry matter) was followed by successive addition of 22.7 g of corn starch (20 g of solids), 3 g of $Na_2HPO_4$ and 25 g of vitamin A acetate (2.19 million IU/g, prepared from vitamin A acetate 2.9 million IU/g and stabilized with 100 mg of ethoxyquin and 14.5 mg of BHT per million IU of vitamin A) while the mixture was emulsified by vigorous stirring at 60° C. The prepared emulsion was sprayed at a temperature of 55° C. using a single-component nozzle under 5.5 to 6.5 bar into a mist of hydrophobic silica in a spraying tower. The still moist product was dried in a vortex drier to a residual moisture content of 5 to 6% and separated from the excess silica. Then 10 g of the resulting powder were heat-treated in a rotating aluminum flask immersed in an oil bath heated to 110° C. Under these conditions, the crosslinking point was 10 minutes. The resulting brown powder had a vitamin A content of 540,000 IU/g with a residual moisture content of 2.9% by weight.

10 g of the as yet uncrosslinked powder were alternatively heated-treated at 120° C. The brown powder resulting under these conditions was no longer dispersible in boiling water after only 7 minutes (=crosslinking point) (particles were maintained completely).

Comparative Examples

Emulsions of the composition indicated in Table 1 were in each case prepared, sprayed to give a powder and dried in the same manner as described in Example 1. The minimum crosslinking times in the heat treatment at 110° C. and 85° C. were determined.

TABLE 1

| Composition of the emulsion | Salt addition | Water content [% by wt] | Minimum crosslinking time at 110° C. [min] | Minimum crosslinking time at 85° C. [min] |
|---|---|---|---|---|
| Comparative: | | | | |
| a) as Ex. 1 | — | 3.1 | >30 | n.d. |
| b) as Ex. 1 | Na acetate | 2.9 | 12 | 190 |
| c) as Ex. 1 | $CaHPO_4$ | 2.1 | 22 | 250 |
| d) as Ex. 1 | $Ca(H_2PO_4)_2$ | 2.3 | 30 | 330 |
| e) as Ex. 1 | $CaSO_4$ | 2.0 | 27 | 260 |
| f) as Ex. 1 | Ca acetate | 2.4 | 11 | 115 |
| The invention: | | | | |
| Example 1 | $Na_2HPO_4$ | 2.9 | 10 | 90 |
| as Ex. 1 | $K_2HPO_4$ | 2.8 | 12 | 100 |

EXAMPLE 2

The fraction of particle size 250 to 355 μm was sieved out of the resulting dry powders in each case prepared as in Example 1 and Comparative Example a), and subjected to a stability test in a standard premix. To do this, about 100 mg of the test samples were weighed into specimen tubes (4 weighings for each sample and testing time), mixed with 4 g of premix consisting of 60% wheat bran, 30% 50% choline chloride on silica and 10% trace element mix consisting of 37.43% $CuSO_4 \times 5\ H_2O$; 46.78% $FeSO_4 \times 7\ H_2O$; 11.79% ZnO; 3.61% MnO and 0.39% $CoCO_3$ and then carefully mixed by hand.

The test samples were stored in open vessels in a climatic chamber with a constant temperature and humidity (40° C. and 70% rel. humidity) for 6 weeks. At the start of storage and after 6 weeks, the 4 test samples prepared for the particular testing time were removed and checked for the remaining content of vitamin A active substance.

The test results are shown in Table 2:

TABLE 2

Investigation of the storage stability of vitamin A dry powders

| Dry powder | t = 0 [I.U./g]*) | t = 6 weeks**) |
|---|---|---|
| 1. of Example 1 | 540,000 = 100% | 80.5% |
| 2. of Comparative Example a) | 520,900 = 100% | 60.4% |

*)Concentration of vitamin A in the dry powder at the start of the stability test.
**)Concentration of vitamin A in the dry powder after storage for 6 weeks. The content was determined by UV spectroscopy. The figure indicates the content of vitamin A relative to the initial concentration.

We claim:

1. A process producing stable dry powders which are insoluble in hot water and which contain one or more lipid-soluble vitamins and/or one or more carotenoids, which comprises the following process steps:

A. preparing an aqueous dispersion containing:
   a1) 2 to 50% by weight of at least one protein,
   a2) 1 to 30% by weight of at least one sugar,
   a3) 0.2 to 20% by weight of $K_2HPO_4$, $Na_2HPO_4$ or a mixture thereof, a4) 0.1 to 20% by weight of at least one lipid-soluble vitamin and/or at least one carotenoid, a5) 5 to 95% by weight of water, where all the % by weight data are based on the total weight of the aqueous dispersion, and the total of the percentage data for the individual components a1) to a5) is 100%, B. converting this dispersion into a dry powder and C. heating the dry powder to a temperature in the range from 55° C. to 180° C., such that the protein is crosslinked to an extent such that the dry powder is insoluble in water for at least 3 minutes after introduction into water at 100° C.

2. A process as claimed claim 1, wherein the aqueous dispersion in process step A contains as an additional component a6) from 0.5 to 20% by weight of starch.

3. A process as claimed claim 1, wherein in process step A a1) 5 to 15% by weight of a gelatin with a bloom value of from 50 to 300, a2) 3 to 15% by weight of at least one sugar selected from the group consisting of fructose and glucose, a3) 0.5 to 5% by weight of $Na_2HPO_4$, a4) 2 to 12% by weight of at least one lipid-soluble vitamin selected from the group consisting of vitamin A, vitamin A acetate, vitamin E and vitamin E acetate, a5) 30 to 85% by weight of water and a6) 1 to 10% by weight of starch are employed.

4. A process as claimed claim 1, wherein the dry powder according to process step B) has a water content in the range from 5 to 15% by weight.

5. A process as claimed claim 1, wherein the dry powder according to process step C) has a water content in the range from 0.1 to 4% by weight.

6. A stable dry powder which is insoluble in hot water according to a process as claimed in claim 1, comprising:

a1) 10 to 70% by weight of at least one protein, a2) 5 to 30% by weight of at least one sugar, a3) 0.5 to 25% by weight of $K_2HPO_4$, $Na_2HPO_4$ or a mixture thereof, a4) 0.1 to 60% by weight of at least one lipid-soluble vitamin and/or at least one carotenoid, a5) 0.1 to 4% by weight of water, where all the % by weight data are based on the total weight of the dry powder, and the total of the percentage data for the individual components a1) to a5) is 100%.

7. A dry powder as claimed in claim 6, comprising as component a2) at least one sugar selected from the group consisting of fructose, glucose and sucrose.

8. A dry powder as claimed in claim 6, comprising as component a6) additionally from 0.5 to 40% by weight of starch.

9. A dry powder as claimed in claim 6, comprising a1) 10 to 70% by weight of a gelatin with a bloom value of from 50 to 300, which is crosslinked to an extent such that it is insoluble in water for at least 3 minutes after introduction into water at 100° C., a2) 5 to 30% by weight of at least one sugar selected from the group consisting of fructose and glucose, a3) 0.5 to 10% by weight of $Na_2HPO_4$, a4) 1 to 50% by weight of a compound selected from the group consisting of vitamin A, vitamin A ester, vitamin E and vitamin E ester and a5) 1 to 3% by weight of water.

10. A human food or animal feed comprising a dry powder as claimed in claim 6.

11. A process as claimed in claim 1, wherein the at least one protein a1) is selected from the group consisting of gelatin, pectin, casein and caseinate.

12. A process as claimed in claim 1 wherein the at least one sugar a2) is selected from for the group consisting of fructose, glucose and sucrose.

13. A process as claimed in claim 1, wherein the at least one lipid-soluble vitamin and/or at least one carotenoid is selected from the group consisting of vitamin A, vitamin A ester, and vitamin E ester.

14. A dry powder as in claimed in claim 6 wherein at least one protein a1) is selected from the group consisting essentially of gelatin, pectin and caseinate.

* * * * *